(12) United States Patent
Needham et al.

(10) Patent No.: US 8,334,778 B2
(45) Date of Patent: *Dec. 18, 2012

(54) REMOTELY CONFIGURABLE ASSISTED-LIVING NOTIFICATION SYSTEM WITH GRADIENT PROXIMITY SENSITIVITY

(75) Inventors: Bradford Needham, North Plains, OR (US); Jean-Manuel Van Thong, Arlington, MA (US); Michael E. Labhard, Lake Oswego, OR (US); James W. Lundell, Portland, OR (US)

(73) Assignee: Intel - GE Care Innovations LLC, Roseville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/270,826

(22) Filed: Oct. 11, 2011

(65) Prior Publication Data

US 2012/0025999 A1 Feb. 2, 2012

(51) Int. Cl.
*G08B 23/00* (2006.01)
(52) U.S. Cl. .................. 340/573.1; 340/540; 340/686.6
(58) Field of Classification Search .............. 340/573.1, 340/567, 540, 692, 546, 522, 505, 686.1, 340/686.6; 379/69
See application file for complete search history.

(56) References Cited

U.S. PATENT DOCUMENTS

| 5,532,680 | A | 7/1996 | Ousborne |
| 5,905,436 | A | 5/1999 | Dwight et al. |
| 5,923,252 | A | 7/1999 | Sizer et al. |
| 6,645,078 | B1 | 11/2003 | Mattice |
| 7,675,503 | B2 * | 3/2010 | Goodwin, III et al. ....... 345/156 |
| 8,035,526 | B2 * | 10/2011 | Needham et al. .......... 340/573.1 |
| 2002/0060630 | A1 | 5/2002 | Power |
| 2004/0257237 | A1 | 12/2004 | Bialecki, Jr. et al. |
| 2005/0035862 | A1 | 2/2005 | Wildman et al. |
| 2006/0066448 | A1 | 3/2006 | Berisford et al. |
| 2006/0261961 | A1 | 11/2006 | Tice |

FOREIGN PATENT DOCUMENTS

| JP | 10-260666 | 9/1998 |
| JP | 11-109936 | 4/1999 |
| JP | 2002-269653 | 9/2002 |

(Continued)

OTHER PUBLICATIONS

International Search Report mailed Apr. 22, 2010, for PCT/US2009/056793.

(Continued)

*Primary Examiner* — Anh V La
(74) *Attorney, Agent, or Firm* — Pillsbury Winthrop Shaw Pittman LLP (57) ABSTRACT

A system provides assisted living messages with varying levels of detail to a person, according to proximity gradients. In one embodiment, the system involves location data. The location data associates first and second notification devices with respective first and second locations at a dwelling. A remote configuration module may enable a caregiver at a location other than the dwelling to specify multiple messages to be presented to the person at the dwelling, to assign first and second messages among the multiple messages to the first location, and to associate the first and second messages with first and second proximities, respectively, for the first location. The first notification device may automatically present the first message in response to detecting the person within the first proximity, and the second message in response to detecting the person within the second proximity. Other embodiments are described and claimed.

11 Claims, 5 Drawing Sheets

FOREIGN PATENT DOCUMENTS

| | | |
|---|---|---|
| JP | 2007-272594 | 10/2007 |
| KR | 2007-0066574 | 6/2007 |
| WO | 03/044755 | 5/2003 |
| WO | 2005/071604 | 8/2005 |
| WO | 2006/094401 | 9/2006 |

OTHER PUBLICATIONS

International Preliminary Report on Patentability issued Mar. 22, 2011, PCT/US2009/056793.

European Search Report dated Dec. 7, 2011.

"Smart Display Device for Independent Living Care," P26789Z, U.S. Appl. No. 61/022,294, filed Jan. 18, 2008.

"Context-Aware Medication Prompting (CAMP) Via Activity Beacon," P26252, U.S. Appl. No. 12/058,998, filed Mar. 31, 2008.

"Methods and Apparatus for Monitoring and Guiding Human Subjects Interacting with Objects" P26788, U.S. Appl. No. 12/215,816, filed Jun. 30, 2008.

Ware, Colin et al.,"Fish Tank Virtual Reality," 1993.

"The Informedix Med-eMonitor Product", www.informedix.com/consumer/AlwaysOn.htm.

"The VoiceZone Reminder", www.braillegifts.com/site/881220/product/MSG-REC.

Describes the QuietCare Product by Living Independently, www.quietcaresystems.com/how_it_works.htm.

Philipose, Matthai, http://seattleweb.intel-research.net/people/matthai/pubs/iccv07.pdf.

Hightower, Jeffrey, "Location Systems for Ubiquitous Computing," seattle.intel-research.net/people/jhightower/pubs/hightower2001location/hightower2001location.pdf, 2001.

The Datasheet for the Sharp GP2Y0A02YK0F, document.sharpsma.com/files/gp2y0a02yk_e.pdf.

MedCenter Monthly Medication Dispenser, http://www.assistedlivingstore.com/p-85-medcenter-monthly-medication-dispenser.aspx.

The Visions System, http://www.thevisionssystem.com/.

\* cited by examiner

REMOTELY CONFIGURABLE ASSISTED-LIVING NOTIFICATION SYSTEM WITH GRADIENT PROXIMITY SENSITIVITY

CROSS-REFERENCE TO RELATED APPLICATIONS

This application is related to and claims the benefit under 35 U.S.C. 120 of co-pending U.S. application Ser. No. 12/284,326, filed on Sep. 19, 2008, the entire contents of which is incorporated herein by reference.

FIELD OF THE INVENTION

The present disclosure relates generally to the field of data processing, and more particularly to methods and related apparatus for providing proximity-sensitive notifications to elders or other people, to provide living assistance.

BACKGROUND

Alzheimer's disease (AD) causes memory loss and other impairments in cognitive function. Consequently, when a person suffers from AD, it may be difficult for that person to live independently. Other conditions may also cause mental or physical impairments which make independent living difficult. Fortunately, tools for assisted living can be used to overcome some of the challenges faced by people who want to live substantially independently, despite physical or mental impairments. Such tools can be simple or complex.

For instance, a caregiver can use sticky notes to post messages around a person's dwelling, to remind that person about various tasks the person should perform (e.g., taking medication, brushing teeth, etc.). Similarly, voice recorders may be used to record messages for a given person, and the messages may be played back manually, for instance in response to the person pressing a "play" button.

Alternatively, an alarm clock may be set to automatically generate an alarm at a specified time, for instance to remind a person to take medication. However, a conventional reminding device (e.g., an alarm clock) may present its message regardless of whether anyone is around.

Outside of the field of health care, a console computer game may use a proximity sensor to detect whether a potential customer is near. When the game is in attract mode, if the game detect a person passing by, the game may respond by playing a predetermined scene or otherwise playing or displaying information to attract the customer to the game.

BRIEF DESCRIPTION OF THE DRAWINGS

Features and advantages of the present invention will become apparent from the appended claims, the following detailed description of one or more example embodiments, and the corresponding figures, in which:

DETAILED DESCRIPTION

An assisted-living notification system may include multiple notification devices positioned in various locations within a dwelling. The notification devices may deliver visual and/or audible messages to the person. For example, as explained in greater detail below, a notification device sitting in the kitchen by a pillbox can provide medication reminders, and a notification device near the exit (e.g., the front door or the rear door) can provide travel reminders or warnings.

In addition, such a device may use a proximity sensor (e.g., a digital passive infrared (PIR) sensor) to detect whether or not a person is near. To save power, the device may switch on the display when the person is close by, and may switch off the display when the person is not around. For instance, the proximity sensor may trigger the reminder device to display its message when the person enters the range of the proximity detector. One or more such reminder devices may be part of an assisted-living notification system that helps a person to live with a significant degree of independence, despite physical or mental impairments.

Such a system may provide appropriate messages or reminders in various circumstances. For instance, at the appropriate time, the system could provide the message that "it's time to take your medications" to help the person remember to take his or her pills. Furthermore, if the system were to detect the person approaching the front door late at night, the system could display a message to "please stay indoors—it is the middle of the night," to help prevent the person from wandering.

If a notification device does not have a proximity detector, or if it has a proximity detector that lacks gradient sensitivity, the designer the notification device may be forced to choose between using a large font size that allows only a short message, and using a small font size that is unreadable at a distance. By contrast, a proximity detector with gradient proximity sensitivity (i.e., that can detect and report different levels of proximity, rather than just the binary sensitivity of proximate or not proximate) can be used to detect how close the person is to the notification device. The notification device can display different messages within a sequence of messages, based on how close the person is to the notification device. For instance, a short message may be displayed in a large font when the person is relatively far from the notification device, and a longer message may be displayed in a smaller font when the person is closer to the notification device.

Figure 1:
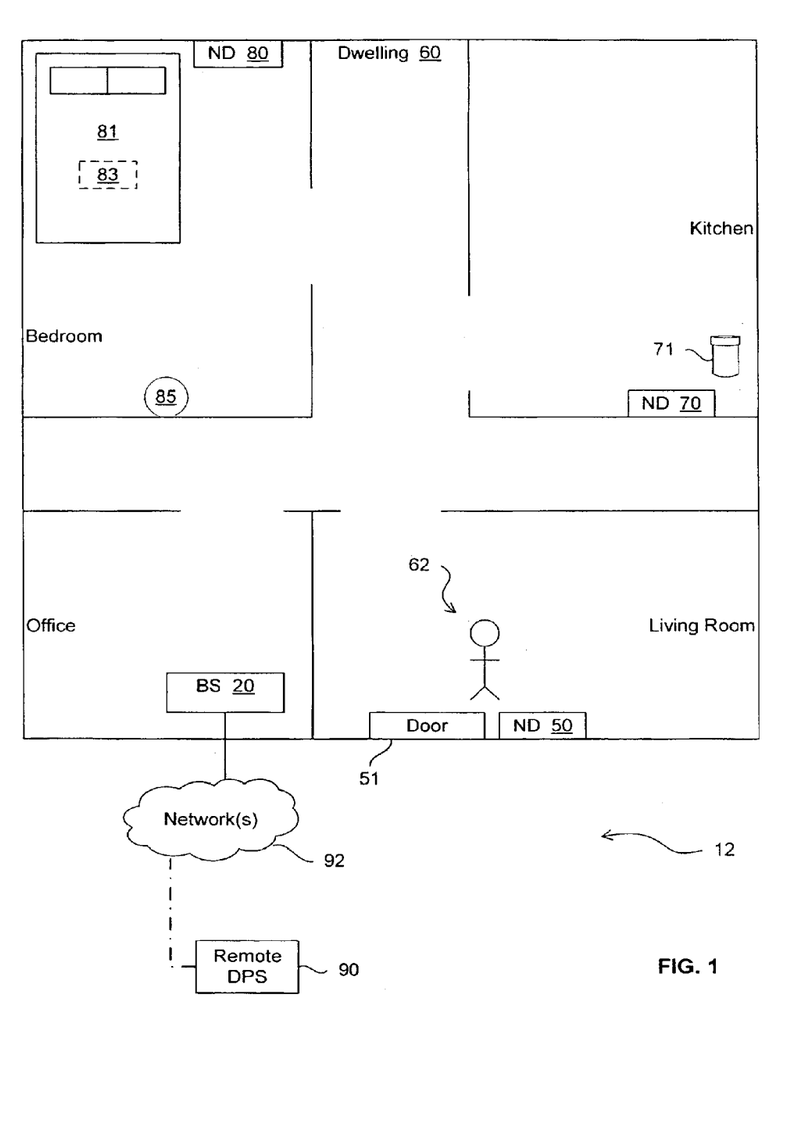
FIG. 1 is a block diagram depicting a suitable data processing environment in which certain aspects of an example embodiment of the present invention may be implemented.

FIG. 1 is a block diagram depicting a suitable data processing environment in which certain aspects of an example embodiment of the present invention may be implemented. The embodiment of FIG. 1 includes a base station 20 situated at the dwelling of a person 62. Base station 20 can send data to and receive data from various external processing systems. For instance, base station 20 can communicate with one or more remote data processing systems 90 via a network 92. Base station 20 also communicates with various notification devices situated at different locations within the dwelling 60. For instance, dwelling 60 includes a notification device 50 in the living room near the front door 51, a notification device 70 in the kitchen near one or more medicine containers 71, and a notification device 80 in the bedroom near the person's bed 81. The various components that work together to provide messages for the person may be referred to collectively as an assisted-living notification system 12.

Figure 2:
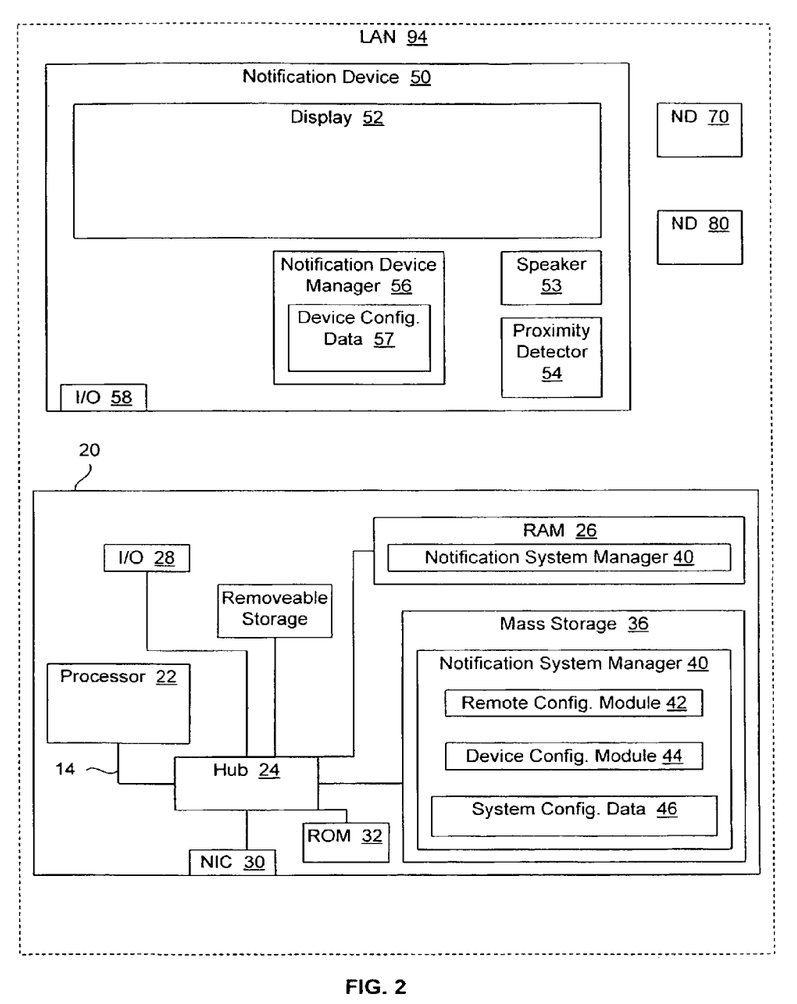
FIG. 2 is a block diagram depicting a base station and a notification device from FIG. 1 in greater detail.

FIG. 2 is a block diagram depicting base station 20 and notification device 50 from FIG. 1 in greater detail. In addition, FIG. 2 illustrates that base station 20 and notification devices 50, 70, and 80 communicate via a local area network (LAN) 94. By contrast, base station 20 communicates with remote data processing system 90 via a wide area network (WAN). LAN 94 and the WAN may use wired and/or wireless connections.

As illustrated, notification device 50 includes one or more output devices such as a display 52 and a speaker 53, as well as a proximity detector 54 and an input/output (I/O) interface 58. A distance measuring sensor unit such as model GP2Y0A02YK0F from Sharp Corporation may be used as proximity detector 54. According to the relevant datasheet, "GP2Y0A02YK0F is a distance measuring sensor unit, composed of an integrated combination of PSD (position sensitive detector), IRED (infrared emitting diode) and signal processing circuit. The variety of the reflectivity of the object, the environmental temperature and the operating duration are not influenced easily to the distance detection because of adopting the triangulation method. This device outputs the voltage corresponding to the detection distance." However, different proximity sensors may be used in other embodiments. For instance, switches in floor mats, in chairs, in the bed, and in other objects around the house can serve as proximity detectors.

Notification device 50 also includes a notification device manager 56 for controlling and/or using display 52, speaker 53, proximity detector 54, and I/O interface 58. Notification device manager 56 may be implemented as computing hardware, software, or a combination of hardware and software for performing the operations described below. In the embodiment of FIG. 2, notification device manager 56 includes device configuration data 57 for specifying or customizing the operating parameters for notification device 50, as described in greater detail below.

In one embodiment, notification device 50 is approximately 5 inches wide, 4 inches tall, and 1 inch deep, and display 52 is approximately 3 inches wide and 1.5 inches tall. Other embodiments can be smaller or larger in any of these dimensions.

In one embodiment, I/O interface 58 allows notification device 50 to communicate with base station 20 wirelessly. Accordingly, I/O interface 58 may include an antenna, a transceiver, an amplifier, and other components to support wireless communication. In other embodiments the base station may communicate with notification devices via a wired connection.

In the embodiment of the FIGS. 1 and 2, notification devices 70 and 80 include the same features as notification device 50. In other embodiments, and assisted-living notification system may use a variety of different notification devices. For example, some notification devices may lack a speaker, and others may lack a display.

Base station 20 may also be referred to as a processing system 20. Processing system 20 has various hardware and software components. The hardware components include a processor 22, random access memory (RAM) 26, and read-only memory (ROM) 32. Processor 22 may include one or more processing units or cores. An alternative processing system may include multiple processors.

Processing system 20 may also include other hardware components, and the hardware components may be communicatively coupled via one or more system buses 14 or other communication pathways or mediums. This disclosure uses the term "bus" to refer to shared (e.g., multi-drop) communication pathways, as well as point-to-point pathways, interconnect rings, etc. In the embodiment of FIG. 1, processing system 20 includes one or more volatile and/or non-volatile data storage devices, such as RAM 26, ROM 32, mass storage devices 36 such as hard drives, and/or other devices or media. For example, processing system 20 may include one or more removable storage devices, such as drives for digital versatile disks (DVDs) or other kinds of optical disks, floppy disk drives, tapes, flash memory, memory sticks, etc. For purposes of this disclosure, the terms "read-only memory" and "ROM" may be used in general to refer to non-volatile memory devices such as erasable programmable ROM (EPROM), electrically erasable programmable ROM (EEPROM), flash ROM, flash memory, etc. Processing system 20 may also have a chipset, a bridge, a hub 24, and/or other modules which serve to interconnect various hardware components.

Processing system 20 may be controlled, at least in part, by input from input devices such as a keyboard, a mouse, a remote control, etc., and/or by directives received from another machine, biometric feedback, or other input sources or signals. Processing system 20 may utilize one or more communication ports and one or more wired or wireless connections to communicate with one or more other data processing systems. Communication ports may also be referred to as I/O ports, and they may be implemented as parallel ports, serial ports, universal serial bus (USB) controllers, high-definition multimedia interface (HDMI) ports, network interface controllers (NICs), modems, etc. For instance, base station 20 may use I/O port 28 to communicate with the notification devices, and may use a NIC 30 to communicate with remote devices such as processing system 90. Alternatively, a single I/O interface may be used for all network connections, or multiple NICs and/or other I/O interfaces may be used.

In various embodiments, processing systems may be interconnected by way of a physical and/or logical network, such as a LAN, a WAN, an intranet, the Internet, etc. Network communications may utilize various wired and/or wireless short range or long range carriers and protocols, including radio frequency (RF), satellite, microwave, Institute of Electrical and Electronics Engineers (IEEE) 802.11, 802.15.4, 802.16, 802.20, Bluetooth, optical, infrared, cable, laser, etc. Protocols for 802.11 may also be referred to as wireless fidelity (WiFi) protocols. Protocols for 802.15.4 may also be referred to as wireless personal area network (WPAN) protocols. Protocols for 802.16 may also be referred to as WiMAX or wireless metropolitan area network protocols, and information concerning those protocols is currently available at grouper.ieee.org/groups/802/16/published.html. For instance, base station 20 may serve as an aggregator, and the notification devices may use the 802.15.4 protocol, the Bluetooth protocol, or any other suitable protocol; to communicate with the base station. In addition, components of a notification device may be distributed (as opposed to integrated into a single housing), and those components may use the 802.15.4 protocol, the Bluetooth protocol, and/or any other suitable protocol to communicate with each other. In another embodiment, the aggregator may reside outside of the dwelling, and the notification devices may access the aggregator via a WAN.

The invention may be described herein with reference to data such as instructions, functions, procedures, data structures, application programs, configuration settings, etc. When the data is accessed by a machine, the machine may respond by performing tasks, defining abstract data types, establishing low-level hardware contexts, and/or performing other operations, as described in greater detail below. The data may be stored in volatile and/or non-volatile data storage. For purposes of this disclosure, the term "program" covers a broad range of software components and constructs, including applications, drivers, processes, routines, methods, modules, and subprograms. The term "program" can be used to refer to a complete compilation unit (i.e., a set of instructions that can be compiled independently), a collection of compilation units, or a portion of a compilation unit. The term "program" may also be used to refer to a set of one or more instructions resulting from processes such as translation, interpretation, compilation, linking, etc. Thus, the term "program" may be used to refer to any collection of instructions which, when executed by a processing system, performs a desired operation or operations.

In the embodiment of FIG. 1, processing system 20 also includes various software resources. For instance, mass storage device 36 contains an OS and at least one program 40. Processing system 20 can copy the OS and program 40 into RAM 26 and execute the OS and program 40 on processor 22. Program 40 may be referred to as a notification system manager 40, and in one embodiment, notification system manager 40 includes various subcomponents, such as a remote configuration module 42 and a device configuration module 44.

Processing system 20 may also store other kinds of data in RAM 26 and/or mass storage 36. For instance, as described in greater detail below, processing system 20 may store system configuration data 46 pertaining to the locations of the various notification devices within the dwelling, the messages to be displayed, etc.

In the embodiment of FIG. 1, system configuration data 46 in base station 20 includes location data that associates each notification device with a particular location within the dwelling. The input that base station 20 receives to establish the system configuration may be entered by a user at base station 20, or by a user at a remote device, such as processing system 90.

As explained in greater detail below, notification system manager 40 allows users to specify messages to be displayed on notification device at a particular location, and notification system manager 40 updates device configuration data 57 within the notification devices to program each device to operate in accordance with the users' specifications. For instance, notification system manager 40 may update the device configuration data 57 in notification device 50 to program notification device 50 with the messages and other operating parameters associated with the exit location.

In alternative embodiments, the processing resources of the assisted-living notification system may be distributed differently. For instance, the proximity detectors need not be integral with the notification devices. The proximity detectors may communicate directly with the base station, and the base station may dynamically determine which messages should be presented by which notification devices, based on the data from the proximity detectors. Alternatively, the base station may be omitted, and each notification device may have its own Internet protocol (IP) address. Remote users may connect directly to the notification devices to configure those devices with desired operating parameters. Other variations may be used in other embodiments.

In one embodiment, device configuration data 57 provides for a variety of modes of display, based on how close the person is to the display. Notification device manager 56 may evaluate the proximity data and choose the mode of display, based on the detected closeness of the person to the display. Notification device manager 56 may also store the previous distances reported by proximity detector 54 and use that proximity data to determine whether the person is getting closer to or further from the display.

For example, notification device 50 might initially show nothing. If the person gets up in the middle of the night and approaches door 51, notification device 50 might just flash. If the person comes within two feet of the door, notification device 50 might show the following text, in a large font: "Please Stay Indoors". If the person comes within one foot of the door, notification device 50 might show a longer text message in a smaller font; e.g., "Please stay inside—it is too late at night for you to be outside."

Thus, assisted-living notification system 12 makes efficient use of a small, inexpensive display by displaying information that can be read at the moment: if the person is at some distance from the display, a display gives a small amount of information in a large font; if the person is closer, the display gives a larger amount of information in a smaller font. Assisted-living notification system 12 may also deliver prompts that are tailored to the person's level of interest at the moment, as indicated by the person's distance from the display.

Figure 3A:
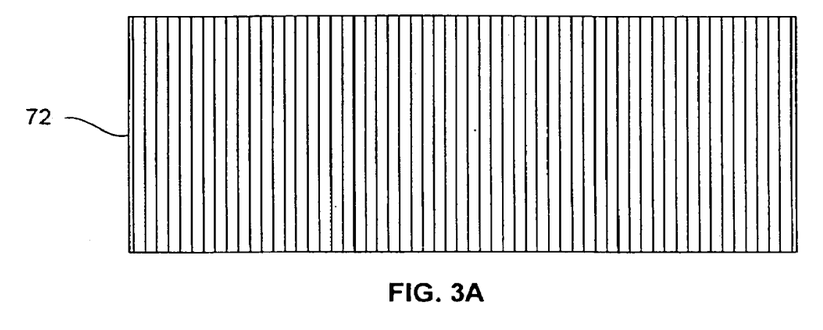
FIGS. 3A-3C depict a sequence of related messages presented for the person by a notification device from FIG. 1.
Figure 3B:
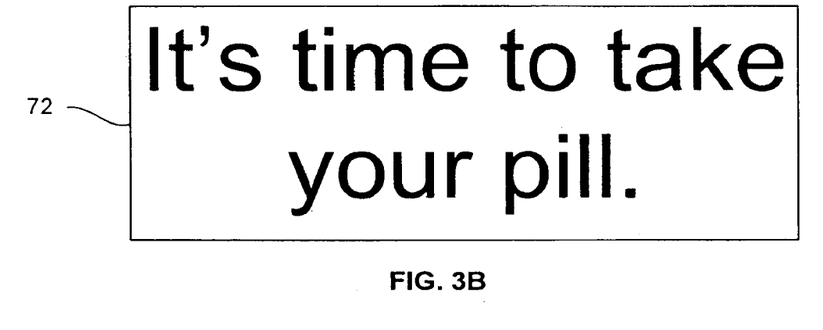
Figure 3C:
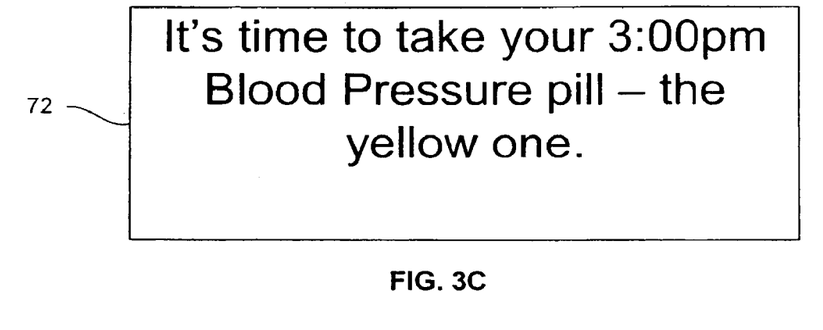

FIGS. 3A-3C depict a sequence of related messages presented for the person by a notification device from FIG. 1. In particular, FIGS. 3A-3C depict messages as presented on a display 72 of notification device 70, which is located in the kitchen near one or more medicine containers 71. If notification device 70 does not detect the person within a minimum proximity to notification device 70, display 72 may remain blank. Then, if notification device 70 detects that the person is within the minimum proximity, notification device 70 causes display 72 to blink. Notification device 70 may detect that the person is within the minimum proximity when the person casually passes by notification device 70, for instance. FIG. 3A shows display 72 filled with vertical bars. Notification device 70 may blink this pattern or any other suitable pattern, including solid white, solid black, or any other color.

If the person stands closer to notification device 70 to learn more, notification device 70 then displays the next message in the sequence, in a large font. For example, as shown in FIG. 3B, display 72 may use a 48 point font to present the text "It's time to take your pill." If the person leans in towards display 72 to learn even more, display 72 presents the next message in the sequence in a smaller font. For instance, as shown in FIG. 3C, display 72 may use a 24 point font to present the text "It is time to take your 3:00 pm Blood Pressure pill—the yellow one."

Figure 4:
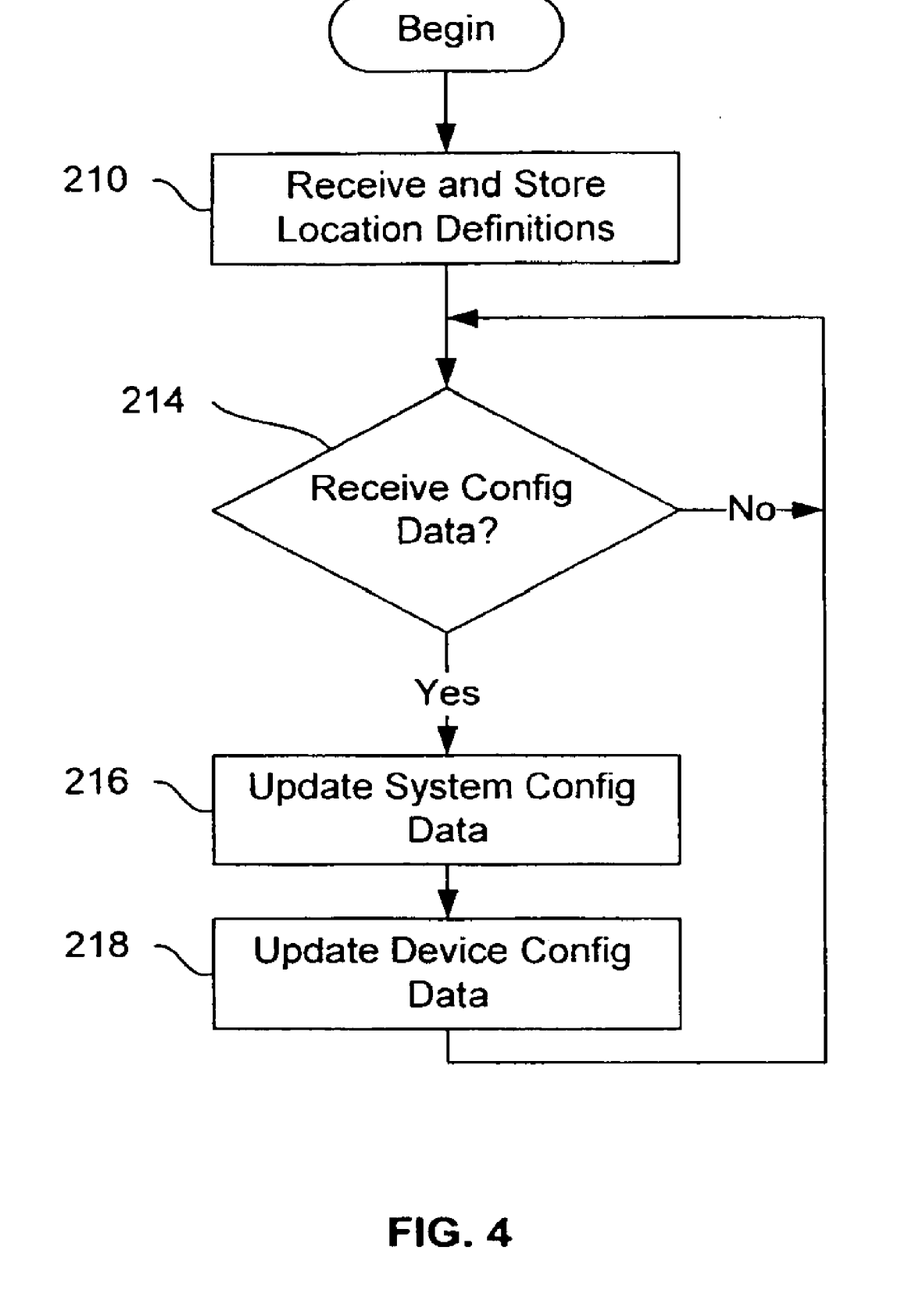
FIG. 4 is a flowchart depicting an example embodiment of a process for configuring an assisted-living notification system, in the context of the data processing environment of FIG. 1.
Figure 5:
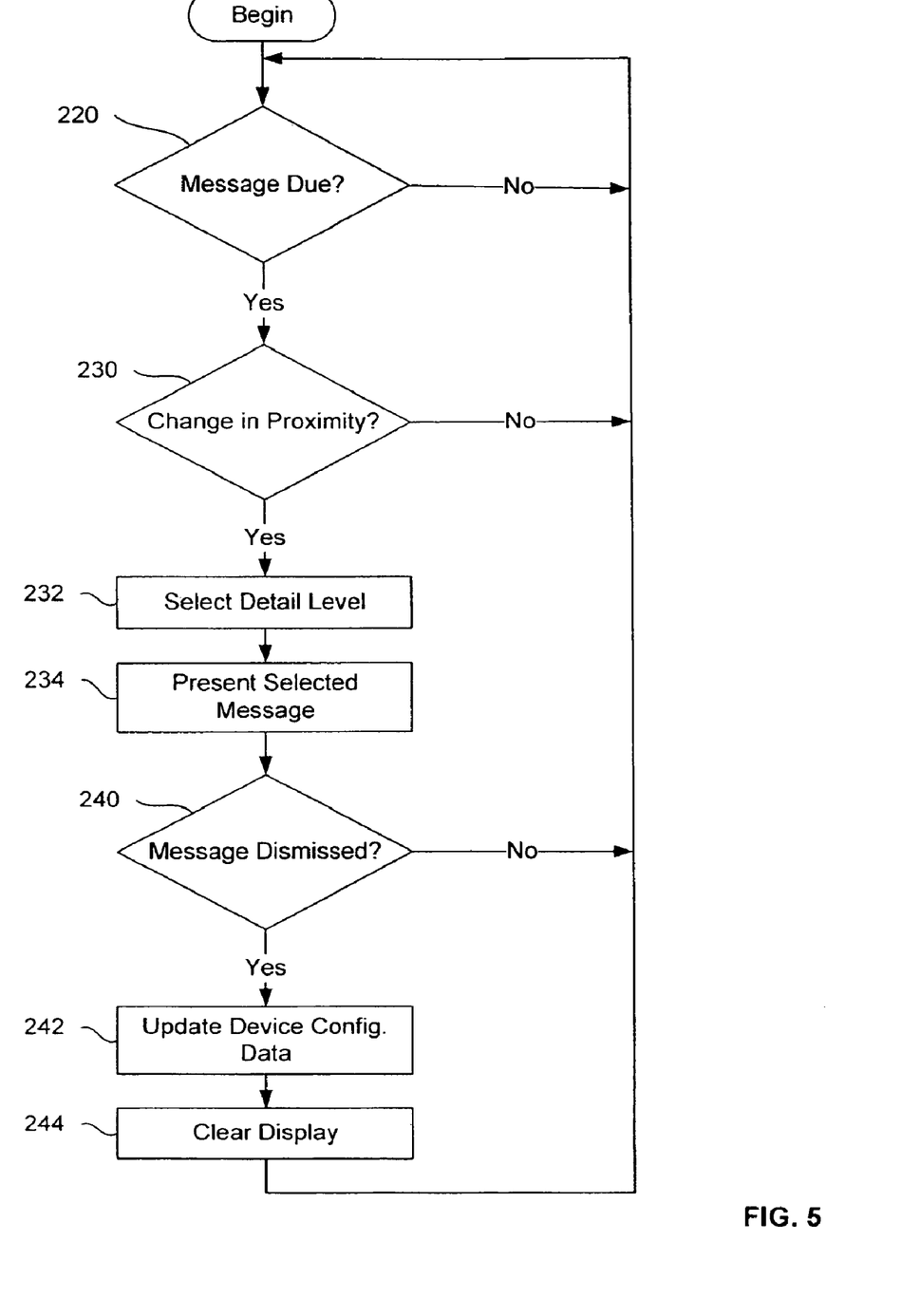
FIG. 5 is a flowchart depicting an example embodiment of a process for using an assisted-living notification system, in the context of the data processing environment of FIG. 1.

FIGS. 4 and 5 are flowcharts depicting an example embodiment of a process for configuring and using an assisted-living notification system, in the context of the data processing environment of FIG. 1. That process may begin after the necessary hardware components have been deployed. For instance, the process may begin after base station 20 and notification devices 50, 70, and 80 have been installed in dwelling 60, as depicted in FIG. 1.

As shown in FIG. 4 at block 210, notification system manager 40 may then receive location definitions that associate each notification device with a particular location within dwelling 60. For instance, a caregiver may program base station 20 with location definitions indicating that notification device 50 is located at the front door 51, notification device 70 is located near medicine containers, and notification device 80 is located near bed 81. Notification system manager 40 may save the location definitions as part of system configuration data 46.

Notification system manager 40 may also allow users to define various events for each location, along with times for those events. For instance, a caregiver may define an "exit warning" event to apply to the notification device associated with front door 51 between the times of 9:00 p.m. and 6:00 a.m. Similarly, the caregiver may define various "medicine reminder" events to apply to the notification device associated with the medicine containers, with each event to cover a specified time period. For purposes of this disclosure, the term "caregiver" refers to a wide range of people, including, without limitation, physicians, nurses, other types of professional health care providers, pharmacists, family members, friends, etc.

Notification system manager 40 may save the event definitions as part of system configuration data 46. In addition, notification system manager 40 may allow users to add, modify, and delete message definitions associated with the events. For instance, as shown at blocks 214 and 216, in response to receiving message definitions, message management module 44 may store those message definitions as part of system configuration data 46. The message definitions may specify the messages to be presented at each notification device.

In at least one embodiment, the proximity detector has gradient proximity sensitivity. That is, the output of the proximity detector changes depending on how close the person is to the proximity detector, with the proximity detector providing at least three different output values. For instance, if no person is detected by the proximity detector, the proximity detector may report a first value corresponding to a proximity of "none" or "undetected." If the proximity detector detects a person at a distance of eight feet or more, the proximity detector may report a second value corresponding to a proximity of "far." If the proximity detector detects a person at a distance between two feet and eight feet, the proximity detector may report a third value corresponding to a proximity of "medium." If the proximity detector detects a person at a distance between two feet and one foot, the proximity detector may report a fourth value corresponding to a proximity of "near." And if the proximity detector detects a person at a distance closer than one foot, the proximity detector may report a fifth value corresponding to a proximity of "very near."

Alternatively, the proximity detector may produce analog output or many different discrete output values corresponding to different proximity ranges, and the notification device may translate the output from the proximity detector into a smaller number of proximity ranges or values (e.g., the three values none, far, and near).

Further, the translation of proximity into ranges may be customizable on a per-device basis. For example, notification device 80 by the bedside may be programmed to read "near" for 10 inches. In contrast, notification device 70 on the kitchen counter might be programmed to read "near" for 30 inches. In one embodiment, each set of proximity ranges could be represented by a table mapping a set of distance thresholds into a set of ranges, in which each row of the table contains a threshold (for example, 10 inches) and a range (for example, "near"). The data for translating distance thresholds into ranges may be referred to as proximity translation definitions. A notification device may save the proximity translation definitions as part of the device configuration data. A notification device could convert a proximity value to a range by scanning the table, finding the smallest proximity value greater than or equal to the proximity value being converted, then reading the associated range.

In other embodiments, other techniques may be used to map a set of proximity values into a smaller set of range names. That is, any suitable component of the system may convert the momentary proximity reading into a proximity range, which is used to choose the form and content of the display and/or audio output to the user.

The message definitions may provide a sequence of messages to be presented for each event, with each message in a particular sequence associated with a particular proximity gradient. For example, for the notification device 50 associated with front door 51, the user may specify a sequence of three messages for the "exit warning" event. The user may link the first message to a "far" proximity gradient, the second message to a "medium" proximity gradient, and the third message to a "close" proximity gradient. The first message may be a simple blinking of display 52. The second message may be the text "Do not go out." And the third message may be the text "Please stay indoors—it is the middle of the night."

Notification system manager 40 may also accept a detailed message, and may then automatically create one or more shorter messages for inclusion in the sequence of messages for the associated event. For instance, a caregiver may specify a long message to be presented at a "near" proximity, and notification system manager 40 may then automatically create a shorter message to be presented at a more distant proximity. In one embodiment, the caregiver may fill out a template of detailed information that notification system manager 40 uses to create the specific messages. For example, the caregiver may enter the times, names, and look of pills to be taken, such as a 3 pm blood pressure pill that is yellow. From this information and its template, notification system manager 40 may create a "far" message that is simply a blinking display; a "medium" generic pill-reminder such as "it's time to take your pill", and a "near" message that uses all the details the caregiver provided, such as "It's time to take your 3 pm blood pressure pill—the yellow one".

Notification system manager 40 may allow users to specify location definitions, event definitions, and message definitions locally (e.g., from base station 20). In addition, remote configuration module 42 provides a remote programming interface that enables users to specify location definitions, proximity translation definitions, event definitions, and/or message definitions from a remote processing system. Location definitions, event definitions, and message definitions may also be referred to as location data, event data, and message data, respectively.

As indicated at block 218, device configuration module 44 may then update the device configuration data in each notification device, to program each device with the events and messages relevant to that device. For instance, device configuration module 44 may update notification device 50 with device configuration data 57 pertaining to the "front door" location. The process may then return to block 214, with notification system manager 40 waiting to receive new message data.

As shown at block 220 of FIG. 5, each notification device may then compare the current time with the times of the events described in the device configuration data of that notification device, to determine whether any messages are currently due to be presented by that notification device. If no messages are currently due, the state of the notification device may remain substantially the same, as indicated by the arrow returning to block 220. If the notification device determines that a message is currently due, the notification device may then determine whether there has been a change in proximity, as indicated at block 230. This determination is made based on the output from the proximity detector of the notification device. Thus, if a message is due, but the notification device does not detect a person, no message is presented.

As indicated at block 232, once a person is detected, the notification device selects the proper message in the sequence of messages for the triggering event, based on the detected proximity gradient. As shown at block 234, the notification device then presents that message. For instance, if notification device 70 determines that a message is due to remind the person to take a pill, when the person enters the kitchen and the proximity detector detects the person at the "far" proximity, notification device 70 may select and present a message associated with the "far" proximity. For example, as shown in FIG. 3A, display 72 may begin blinking.

This document explains that notification devices present messages to a person. In one embodiment, text or other visual messages are presented in a display. In another embodiment, a speaker is used to present messages audibly. Other embodiments may present both visual messages and audible messages. Likewise, caregivers can specify whether messages are to be presented visibly, audibly, or both. For instance, for an exit-warning event, a caregiver can provide a text message to be displayed when the person is at a "medium" proximity to the front door and an audible message to be played when the person is at a "near" proximity.

Referring again to FIG. 5, as shown at block 240, notification device may then determine whether the person has dismissed the message. For instance, the medicine container may include a sensor and logic to automatically send a dismiss signal to the notification device when the container is opened. In addition or alternatively, the notification device may include one or more keys, a touch-sensitive screen, or any other suitable mechanism for accepting user input, and person may use that input mechanism to dismiss the message. For ease of reference, all such input mechanisms may be referred to as "buttons."

In addition to a "dismiss" button, a notification device may include a "play" button and other buttons. When the "play" button is pressed, the notification device may play an audible message associated with the due event.

In another example, a device by the door may be programmed to blink when a person is far away, show a large question-mark icon when a person is at a medium distance, and, when a person is near, play a recorded audio reminder "remember to pick up the refill of your pills at the pharmacy . . . . I ordered them on Wednesday and they called to let you know the pills are in". In this case, a written message might be too long or might be confusing, so the detailed message is delivered in audio instead. In this case, the message can be recorded through a microphone on the sender's PC, then uploaded to the system from that PC.

Alternatively, if the person who is to receive the message has some vision impairments, such as macular degeneration or tunnel vision, the "far" message may be a beep, the "medium" message might be a faster beep, and the "near" message might be a Text-To-Speech audio message based on the programmed text.

In a multi-person household, the "far" message may be a blink or beep, the "medium" message might by the printed or spoken name of the person the message is directed at, and the "near" message might be the complete message. A person other than the intended recipient might pass by close enough to see another person's name, but not stand near enough to the device to receive the complete message.

As shown at blocks 242 and 244, if the message has been dismissed, the notification device may clear its display and update its device configuration data to indicate that the message is no longer due. The process may then return to block 220.

However, if the message is still due and the proximity of the person has changed to a different gradient, the notification device may select a new level of detail for the message and may present that new message, as indicated at blocks 220, 230, 232, and 234. For instance, if the person has moved to a position three feet away from the proximity detector, the notification device may select and display the message associated with the "medium" proximity. For example, the notification device may display a reminder like that shown in FIG. 3B. Similarly, if the person approaches within two feet of the notification device, the notification device may display a message like that shown in FIG. 3C.

Notification device 50 may operate in the same manner to present messages associated with the front door. For instance, notification device 50 may change from presenting nothing to blinking when a person is detected at a far range; then to presenting the message "Please stay indoors" if the person comes within 2 feet of the door; and then to presenting a longer message in a smaller font if the person comes within one foot of the door.

Assisted-living notification system 12 may be used to provide many different kinds of messages, including medication reminders, messages for safety ("don't open the door to strangers"), messages for comfort ("how to dress for bed"), and messages for reassurance ("you're living in your daughter Judy's house—we are happy to have you here"). Assisted-living notification system 12 makes it easy for a caregiver to place location-specific reminders around the house. Furthermore, the remote programming interface allows caregivers to add, modify, and delete such messages from a remote computer.

For example, suppose that Joan, a person with dementia, lives alone. Her daughter/caregiver, Anne, has placed notification device 50 by the front door. When Ann wants Joan to remember something before going out, Ann remotely records the message via her PC (e.g., remote data processing system 90) and sends the message to notification device 50, causing a light on notification device 50 to blink slowly. As Joan approaches the front door, she sees the blinking light on notification device 50 and presses its "play" button, causing notification device 50 to play the audio message. An example message is "remember to refill your heart pills" or "remember to wear your coat—it's cold out."

Furthermore, messages can be provided by multiple authorized people. For example, Joan's pharmacist could configure one or more of Joan's notification devices with an event with the message "it's time to pick up your pills." Any suitable approach may be used to prevent unauthorized people from providing messages or otherwise changing the configuration of assisted-living notification system 12.

As indicated above, in some embodiments, one or more of the components of a notification device may be distributed. For example, one embodiment may use presence sensed at discrete locations in the house to calculate proximity. Presence may be sensed at least in part by detectors separate from the notification devices. So, for example, a pressure switch 83 in bed 81 may indicate presence in the bed, from which the system can infer that the person is at proximity "Near" to bedroom notification device 80. Similarly, the system may include a passive-infrared motion detector 85 in the bedroom, such as is commonly used in burglar alarms. Output from motion detector 85 indicates presence in the bedroom; and in the absence of other sensory input, assisted-living notification system 12 may infer that someone is in the bedroom, at proximity "far" from notification device 80. A network of such activity sensors may be used to infer location or activity (e.g., "making lunch") of a person within the house. Furthermore, such location inferences may be used to infer proximity of a person to the various notification devices, thereby causing the notification devices to present messages when appropriate. For example, if a location-estimation system containing the Cartesian coordinates of the notification devices has calculated the Cartesian location of a person in dwelling 60 (e.g., in the living room, 3 feet from the bottom wall in FIG. 1 and 2 feet from the right wall in that figure), the location-estimation system could calculate the linear distance (proximity) from notification device 50 to the person, then provide that notification device with the calculated proximity. Similarly, if a location-estimation system containing the Cartesian bounds and orientation of the bed received a message from a bed occupancy switch 83 indicating that the bed 81 was occupied, that system could calculate the likely distance (proximity) from the head of the person in the bed to the bedroom notification device 80, and provide that notification device with the calculated proximity.

In light of the principles and example embodiments described and illustrated herein, it will be recognized that the illustrated embodiments can be modified in arrangement and detail without departing from such principles. For instance, some or all of the hardware and techniques described herein could be used in a grocery store to deliver varied levels of advertising, in an office to deliver office-related messages, at a school, or at other places where intended recipients of messages move about. For example, a notification device in a grocery store could present a sequence of messages such as (a) blinking, (b) "Sale," and (c) "Today Only: Round Tip Steak—Buy 1 Get 1 Free," in response to detecting a person at far, medium, and near ranges, respectively. Similarly, a notification device in an office, temporarily placed near a printer, could present the following sequence of messages: "Broken," "No Paper Feed," and "10:15 am September 20—printer doesn't feed paper, despite refilling."

Also, the foregoing discussion has focused on particular embodiments, but other configurations are contemplated. In particular, even though expressions such as "in one embodiment," "in another embodiment," or the like are used herein, these phrases are meant to generally reference embodiment possibilities, and are not intended to limit the invention to particular embodiment configurations. As used herein, these terms may reference the same or different embodiments that are combinable into other embodiments.

Similarly, although example processes have been described with regard to particular operations performed in a particular sequence, numerous modifications could be applied to those processes to derive numerous alternative embodiments of the present invention. For example, alternative embodiments may include processes that use fewer than all of the disclosed operations, processes that use additional operations, processes that use the same operations in a different sequence, and processes in which the individual operations disclosed herein are combined, subdivided, or otherwise altered.

Alternative embodiments of the invention also include machine accessible media encoding instructions for performing the operations of the invention. Such embodiments may also be referred to as program products. Such machine accessible media may include, without limitation, storage media such as floppy disks, hard disks, CD-ROMs, ROM, and RAM; and other detectable arrangements of particles manufactured or formed by a machine or device. Instructions may also be used in a distributed environment, and may be stored locally and/or remotely for access by single or multi-processor machines.

It should also be understood that the hardware and software components depicted herein represent functional elements that are reasonably self-contained so that each can be designed, constructed, or updated substantially independently of the others. The control logic for providing the functionality described and illustrated herein may be implemented as hardware, software, or combinations of hardware and software in different embodiments. For instance, one or more modules, subsystems, etc., in one or more devices may be implemented as embedded controllers, using components such as programmable or non-programmable logic devices or arrays, application-specific integrated circuits (ASICs), embedded processors, smart cards, and the like.

As used herein, the terms "processing system" and "data processing system" are intended to broadly encompass a single machine, or a system of communicatively coupled machines or devices operating together. Example processing systems include, without limitation, distributed computing systems, supercomputers, high-performance computing systems, computing clusters, mainframe computers, mini-computers, client-server systems, personal computers, workstations, servers, portable computers, laptop computers, tablets, telephones, personal digital assistants (PDAs), handheld devices, entertainment devices such as audio and/or video devices, and other platforms or devices for processing or transmitting information.

In view of the wide variety of useful permutations that may be readily derived from the example embodiments described herein, this detailed description is intended to be illustrative only, and should not be taken as limiting the scope of the invention. What is claimed as the invention, therefore, is each implementation that comes within the scope and spirit of the following claims, and all equivalents to such implementations.

What we claim is:

1. A notification apparatus for providing assisted-living messages with varying levels of detail to a person according to proximity gradients, the apparatus comprising:
   a communication interface device configured to receive a first message and a second message from a remote configuration device, wherein the notification apparatus is configured to determine whether the first message is associated with a first proximity and whether the second message is associated with a second proximity; and
   a display configured to (a) automatically present the first message in response to detecting a person within the first proximity to the notification apparatus and (b) automatically present the second message in response to detecting a person within the second proximity to the notification apparatus.

2. The notification apparatus according to claim 1, wherein the notification apparatus is configured to determine whether to display at least part of the first message with a first font size and whether to display at least part of the second message with a second font size, wherein the first font size is bigger than the second font size, and wherein the second proximity is indicative of a near proximity and the first proximity is indicative of a far proximity.

3. The notification apparatus according to claim 1, wherein the notification apparatus is configured to detect a person within the first proximity or the second proximity to the notification apparatus by receiving a proximity measurement from a proximity sensor.

4. The notification apparatus according to claim 1, wherein the communication interface device is further configured to receive an event definition that defines an event, and wherein the notification apparatus is configured to display the first message only if the event has been detected and is configured to display the second message only if the event has been detected.

5. A method for providing assisted-living messages with varying levels of detail to a person according to proximity gradients, comprising:
- receiving, at a notification device, a first message and a second message from a remote configuration device;
- determining whether the first message is associated with a first proximity and whether the second message is associated with a second proximity; and
- detecting a person within a first proximity or a second proximity to the notification apparatus;
- displaying, on a display device of the notification device, (a) the first message in response to detecting the person within the first proximity to the notification apparatus and (b) the second message in response to detecting the person within the second proximity to the notification apparatus.

6. The method according to claim 5, further comprising determining whether to display at least part of the first message with a first font size and whether to display at least part of the second message with a second font size, wherein the first font size is bigger than the second font size, and wherein the second proximity is indicative of a near proximity and the first proximity is indicative of a far proximity.

7. The method according to claim 5, wherein detecting the person within the first proximity or the second proximity to the notification apparatus comprises receiving a proximity measurement from a proximity sensor.

8. The method according to claim 5, further comprising receiving an event definition and determining whether an event defined in the event definition has occurred.

9. A method for providing assisted-living messages, comprising:
- receiving, at a device configuration apparatus in a dwelling, location data that associates a first notification apparatus in the dwelling with a first location in the dwelling;
- receiving, at the device configuration apparatus, event data that defines an event for the first notification device;
- receiving, from a caregiver at a location other than the dwelling, a first message and a second message associated with the event;
- associating the first message with a first proximity;
- associating the second message with a second proximity;
- transmitting the first message to the first notification device;
- transmitting the second message to the first notification device;
- transmitting a proximity translation definition to the first notification device, wherein the proximity translation definition associates the first message with the first proximity and associates the second message with the second proximity.

10. The method according to claim 9, wherein the location data further associates a second notification apparatus in the dwelling with a second notification apparatus in the dwelling.

11. The method according to claim 9, further comprising transmitting at least part of the event data to the first notification device.

* * * * *

UNITED STATES PATENT AND TRADEMARK OFFICE
CERTIFICATE OF CORRECTION

| | |
|---|---|
| PATENT NO. | : 8,334,778 B2 |
| APPLICATION NO. | : 13/270826 |
| DATED | : December 18, 2012 |
| INVENTOR(S) | : Bradford Needham et al. |

It is certified that error appears in the above-identified patent and that said Letters Patent is hereby corrected as shown below:

On title page, after Item (65) Prior Publication Data,
add the following priority section:
--Item (63) Related U.S. Application Data, Continuation of application No. 12/284,326, filed on Sept. 19, 2008, now Pat. No. 8,035,526.--

Signed and Sealed this
Twenty-sixth Day of March, 2013

Teresa Stanek Rea
*Acting Director of the United States Patent and Trademark Office*